United States Patent
Fujiwake et al.

(10) Patent No.: US 6,566,141 B2
(45) Date of Patent: May 20, 2003

(54) METHOD OF DETECTING MUTATION IN BASE SEQUENCE OF NUCLEIC ACID

(75) Inventors: Hideshi Fujiwake, Kyoto (JP); Tomoko Yamaguchi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/827,908

(22) Filed: Apr. 9, 2001

(65) Prior Publication Data

US 2001/0046678 A1 Nov. 29, 2001

(30) Foreign Application Priority Data

Apr. 25, 2000 (JP) ........................................ 2000-124771

(51) Int. Cl.[7] ............................................. G01N 33/483
(52) U.S. Cl. ......................................... 436/94; 435/91.2
(58) Field of Search ............................. 436/94; 435/91.2

(56) References Cited

PUBLICATIONS

Wallace et al (1981) Nucleic Acids Research 9:879–894.*
Bohling et al (1999) American J. Pathology 154:97–103.*
Akey et al (2001) Biotechniques 30:358–367.*
Germer et al (1999) Genome Research 9:72–78.*
Gross et al (1999) Human Genetics 105:72–78.*
Fujiwara et al (1997) Biochemistry 36:1544–1550.*

* cited by examiner

*Primary Examiner*—Remy Yucel
*Assistant Examiner*—Bronwen M. Loeb
(74) *Attorney, Agent, or Firm*—Rader Fishman & Grauer, PLLC

(57) ABSTRACT

A solution containing double stranded nucleic acid is heated, thereby dissociating the strands, which in turn are cooled and rebounded. A homoduplex and a heteroduplex are formed when the double stranded nucleic acid is a hetero body, while only a homoduplex is formed when the double stranded nucleic acid is a homo body. The temperature of the solution is increased while measuring ultraviolet absorption, thereby acquiring a thermal melting profile. When the heated and cooled solution contains only a homoduplex, the thermal melting profile has a single Tm temperature or two Tm temperatures close to each other. When the heated and cooled solution contains a homoduplex and a heteroduplex, the thermal melting profile has two separate Tm temperatures or further single Tm temperatures close to each other. The method therefore allows for the detection of a heteroduplex or a mutation in a sample double stranded nucleic acid.

7 Claims, No Drawings

METHOD OF DETECTING MUTATION IN BASE SEQUENCE OF NUCLEIC ACID

BACKGROUND OF THE INVENTION

1. Field of the Invention

The present invention relates to a method of detecting mutation in the base sequence of nucleic acid including DNA (deoxyribonucleic acid) and RNA (ribonucleic acid).

2. Description of the Prior Art

It has been clarified that many cancers and genetic diseases are caused by mutation in the base sequence of DNA. The mutation in the base sequence is generally monobasic substitution. A number of methods have been proposed in the technical field of detecting such mutation in the base sequence. Some of the methods shall now be illustrated.

1) DNA (RNA) Sequencing:

The base sequence of a substance to be analyzed is directly analyzed and decided.

2) DNA Chip:

A number of oligonucleotides are fixed onto a glass surface and selectively hybridized with a substance to be analyzed such as a DNA fragment for thereafter detecting a signal based on the hybridization, generally a fluorescent signal, and comparing the same with a normal one thereby estimating the sequence of the substance.

3) SSCP (Single Strand Conformation Polymorphism) Method:

Double stranded DNA (RNA) employed as a sample is dissociated into single stranded DNA for thereafter detecting difference of the higher-order structure of the single stranded DNA, having a specific higher-order structure depending on the base sequence, by polyacrylic amide gel electrophoresis through difference of mobility depending on the higher-order structure, thereby estimating presence/absence of monobasic substitution.

4) DGGE (Denaturing Gradient Gel Electrophoresis) Method:

A sample of a PCR (polymerase chain reaction) product is electrophoresed in a polyacrylic amide gel formed with a concentration gradient of a denaturant for comparing dissociation from double stranded DNA into single stranded DNA at a migration speed and detecting presence/absence of monobasic substitution in the sample.

5) DHPLC (Denaturing High Performance Liquid Chromatography) Method:

Sample double stranded DNA and standard double stranded DNA having standard base sequence with respect to its inspected site are mixed with each other, thermally denatured to be dissociated into single strands and thereafter cooled to be re-bonded to double strands. When the sample double stranded DNA has standard base sequence, only a homoduplex having hydrogen bonds formed on all corresponding bases is formed. When monobasic substitution is present on the inspected site of the sample double stranded DNA, a homoduplex and a heteroduplex having a mismatch site formed with no hydrogen bond between parts of corresponding bases are formed. The heteroduplex has a smaller number of hydrogen bonds than the homoduplex. Therefore, presence of the heteroduplex is detected with a high-speed liquid chromatograph through the fact that the melting temperature (Tm temperature: temperature at which 50% of the total concentration of double stranded DNA is denatured to single stranded DNA) of the heteroduplex is lower than that of the homoduplex, for detecting presence/absence of monobasic substitution.

However, the aforementioned conventional methods have the following disadvantages:

1) Although the DNA sequencing is most reliable, a high cost is disadvantageously required for a series of operations. Further, a large-scale automation line is necessary for improving the throughput.

2) The DNA chip itself is extremely high-priced and the number of oligonucleotides fixed onto the chip must be varied with the substance, disadvantageously leading to a high cost.

3) and 4) In each of the SSCP method and the DGGE method, electrophoretic conditions must be studied every sample, while the composition of the electrophoretic gel must also be studied every sample in the DGGE method. Furthermore, in each of these methods, it is disadvantageously difficult to improve the throughput due to the employment of gel electrophoresis.

5) The DHPLC method disadvantageously requires a high-priced liquid chromatograph.

SUMMARY OF THE INVENTION

An object of the present invention is to provide a method of detecting mutation in the base sequence of nucleic acid capable of performing high-throughput analysis with no requirement for a high-priced apparatus.

The present invention comprises the following steps (A) to (C) for detecting mutation in the base sequence of nucleic acid:

(A) heating a solution containing double stranded nucleic acid employed as a sample for dissociating the double stranded nucleic acid into single stranded nucleic acid, and cooling and rebonding the same into double stranded nucleic acid, (B) increasing the temperature of the solution after completion of the step (A) until the double stranded nucleic acid is dissociated into single stranded nucleic acid for measuring ultraviolet absorption of the solution and acquiring a thermal melting profile, and (C) determining presence/absence of mutation in the base sequence of the double stranded nucleic acid on the basis of the thermal melting profile.

Throughout the specification, the term "double stranded nucleic acid" includes a DNA/DNA double strand (a double strand of single stranded DNA; referred to as double stranded DNA), an RNA/DNA double strand (a double strand consisting of single stranded RNA and single stranded DNA), an RNA/RNA double strand (a double strand of single stranded RNA) and fragments thereof.

The foregoing and other objects, features, aspects and advantages of the present invention will become more apparent from the following detailed description of the present invention.

DESCRIPTION OF THE PREFERRED EMBODIMENTS

When the quantity of double stranded nucleic acid employed as a sample is small, it is preferable to amplify the double stranded nucleic acid by, for example, PCR amplification so that a thermal melting profile can be sufficiently acquired by measuring ultraviolet absorption described afterward. The amplified substance is purified if necessary.

When a solution containing the double stranded nucleic acid employed as a sample is heated for dissociating the double stranded nucleic acid into single strands and the single strands are cooled and rebonded in a step (A), a homoduplex and a heteroduplex are formed as follows if the double stranded nucleic acid (template DNA) employed as the sample is a hetero body. The term "hetero body" stands for a substance including a plurality of types of double stranded nucleic acid having sites different from each other present on parts of the base sequence of an inspected site.

| Template DNA | Homoduplex | Heteroduplex |
|---|---|---|
| AGTA<u>A</u>TA | AGTA<u>A</u>TA | AGTA<u>A</u>TA |
| TCAT<u>T</u>AT | TCAT<u>T</u>AT | TCAT<u>A</u>AT |
| AGTA<u>T</u>TA | AGTA<u>T</u>TA | AGTA<u>T</u>TA |
| TCAT<u>A</u>AT | TCAT<u>A</u>AT | TCAT<u>T</u>AT |

When the double stranded nucleic acid employed as the sample is a homo body, only a homoduplex is formed by dissociation of the double stranded nucleic acid caused by heating and rebonding by cooling. The term "homo body", which is the antonym to "hetero body", stands for a substance consisting of only double stranded nucleic acid having the same base sequence of an inspected site. In order to form a heteroduplex when the base sequence of the inspected site is mutational also when the double stranded nucleic acid employed as the sample is a homo body, it is preferable to add a standard PCR product (standard double stranded nucleic acid) having standard base sequence with respect to the inspected site of the double stranded nucleic acid to the solution containing the double stranded nucleic acid employed as the sample before heating and cooling. Thus, only a homoduplex is formed when the base sequence of the double stranded nucleic acid is normal and identical to that of the standard PCR product, while a homoduplex and a heteroduplex are formed when mutation, e.g. monobasic substitution, is present in the base sequence of the double stranded nucleic acid and the base sequence is different from that of the standard PCR product.

Thereafter the temperature of the solution containing only the homoduplex or the solution containing the homoduplex and the heteroduplex is increased for measuring ultraviolet absorption of the solution thereby acquiring a thermal melting profile in a step (B). It is known that nucleic acid exhibits different quantities of light absorption in the ultraviolet region in a double stranded state and a single stranded state and the quantity of light absorption in the ultraviolet region is larger in the single stranded state as compared with the double stranded state. For example, when slowly (0.5 to 1.0° C./min.) heating certain double stranded nucleic acid and monitoring the quantity of light absorption at a wavelength of 260 nm, a characteristic sigmoidal curve depending on the size and base sequence of the double stranded nucleic acid is obtained (refer to "Gene and Biotechnology" by Naomi Sugimoto, Maruzen Kabushiki Kaisha, first edition issued on Oct. 25, 1999, pp. 10 to 12). The curve is referred to as a thermal melting profile. The thermal melting profile is obtained since hydrogen bonds between base pairs of the double stranded nucleic acid are broken by externally applied thermal energy and the double stranded nucleic acid is gradually converted to a single stranded state.

An inflection point of the thermal melting profile corresponds to the Tm temperature (melting temperature). The Tm temperature depends on the size and base sequence of the double stranded nucleic acid. The heteroduplex includes a mismatch site partially formed with no hydrogen bond between corresponding bases and has a smaller number of hydrogen bonds as compared with the homoduplex, and hence it is predicted that the heteroduplex has a lower Tm temperature than the homoduplex.

It is possible to theoretically predict the Tm temperature from the size and base sequence of the nucleic acid at present, and a program such as MELT94 (disclosed on the Internet (http://web.mit.edu/biology/dna) can be utilized for this prediction.

Thereafter a determination is made as to whether or not the base sequence is mutational from the obtained thermal melting profile in a step (C). When the heated and cooled double strand includes only the homoduplex, the thermal melting profile has one or two Tm temperatures. While the thermal melting profile theoretically has two Tm temperatures if two types of homoduplexes are present, the two Tm temperatures may be experimentally unfindable if the Tm temperatures are close to each other.

When the heated and cooled double strand includes the homoduplex and the heteroduplex, a thermal melting profile having at least two Tm temperatures is obtained. While the thermal melting profile theoretically has four Tm temperatures since two types of homoduplexes and two types of heteroduplexes are present, three or more Tm temperatures may be experimentally unfindable if two Tm temperatures resulting from the homoduplexes or the heteroduplexes are close to each other.

Whether or not a heteroduplex is present in the heated and cooled double strand can be determined by comparing the obtained thermal melting profile with a known thermal melting profile of a homoduplex. In order to simplify this determination, it is preferable to primarily differentiate the thermal melting profile with absorbance for obtaining an inflection point, i.e., the Tm temperature, and determining presence/absence of the heteroduplex on the basis of the Tm temperature itself or the number thereof.

Thus, mutation in the base sequence of nucleic acid can be detected in a shorter time as compared with electrophoresis with no requirement for a high-priced apparatus.

The double stranded nucleic acid from which presence of a heteroduplex is detected by the present invention is preferably subjected to sequencing, in order to decide the site of the mutation in the base sequence. While sequencing must be performed for deciding the site of the mutation in the base sequence, a great deal of analysis time is required if such sequencing is performed as to all samples. When selecting a sample to be subjected to sequencing according to the present invention, the analysis time can be reduced, the cost can also be reduced and the throughput can be improved.

Although the present invention has been described in detail, it is clearly understood that the same is by way of illustration and example only and is not to be taken by way of limitation as the spirit and scope of the present invention are limited only by the terms of the appended claims.

What is claimed is:

1. A method of detecting mutation in the base sequence of a nucleic acid, comprising steps of:
   (A) heating a solution containing a sample double stranded nucleic acid that may be a hetero body, and thereby dissociating the double stranded nucleic acid in the sample into single stranded nucleic acid, and cooling and rebonding the same into double stranded nucleic acid;
   (B) increasing the temperature of the solution after completion of step (A) until the double stranded nucleic acid is dissociated into single stranded nucleic acid while measuring ultraviolet absorption of the solution and acquiring a thermal melting profile; and (C) comparing the thermal melting profile with a known thermal melting profile of a homoduplex, and determining whether a heteroduplex is present in the solution after step (A), thereby determining presence/absence of mutation in the base sequence of the double stranded nucleic acid.

2. The method of detecting mutation according to claim 1, further including a step of mixing with the solution a standard double stranded nucleic acid having standard base sequence with respect to a site in the double stranded nucleic acid to be inspected before heating the solution according to the step (A).

3. The method of detecting mutation according to claim 1, wherein the double stranded nucleic acid is a PCR product.

4. The method of detecting mutation according to claim 1, wherein determination of presence/absence of mutation in the base sequence based on the thermal melting profile is made on the basis of the number of inflection points of the thermal melting profile in the step (C).

5. The method of detecting mutation according to claim 1, wherein determination of presence/absence of mutation in the base sequence based on the thermal melting profile is made on the basis of a melting temperature in the step (C).

6. The method of detecting mutation according to claim 1, which further comprises obtaining an inflection point by determining the derivative of the thermal melting profile with respect to absorbance for determining presence/absence of mutation in the base sequence on the basis of the thermal melting profile in the step (C).

7. The method of detecting mutation according to claim 2, wherein either one or both of the double stranded nucleic acid and the standard double stranded nucleic acid are PCR products.

* * * * *